United States Patent [19]

Howie et al.

[11] Patent Number: 4,639,439

[45] Date of Patent: Jan. 27, 1987

[54] CONTRACEPTIVE COMPOSITION

[75] Inventors: Peter W. Howie, Monifieth; Alan McNeilly, Galashiels, both of England

[73] Assignee: Societe d'Etudes Scientifiques et Industrielles de l'Ile de France, Paris, France

[21] Appl. No.: 786,328

[22] Filed: Oct. 10, 1985

[30] Foreign Application Priority Data

Oct. 10, 1984 [EP] European Pat. Off. ........ 84402033.9

[51] Int. Cl.$^4$ .............................................. A61K 31/56
[52] U.S. Cl. .................................................... 514/171
[58] Field of Search .......................................... 514/171

[56] References Cited

U.S. PATENT DOCUMENTS 4,067,975  1/1978  Yu et al. ............................... 514/171
4,512,987  4/1985  Schendlery ........................ 514/171

*Primary Examiner*—Elbert L. Roberts
*Attorney, Agent, or Firm*—Fitzpatrick, Cella Harper & Scinto

[57] ABSTRACT

The invention relates to a contraceptive composition of a prolactin elevating benzamide, such as N-[(1-ethyl-2-pyrrolidinyl)methyl]2-methoxy 5-sulfamoyl benzamide, and a progestogen.

10 Claims, No Drawings

CONTRACEPTIVE COMPOSITION

BACKGROUND OF THE INVENTION

The invention relates to a contraceptive composition of a prolactin elevating benzamide, such as sulpiride or N-[(1-ethyl-2-pyrrolidinyl) methyl]2-methoxy 5-sulfamoyl benzamide, and a progestogen.

Benzamides, such as sulpiride, are primarily known for their psychotropic properties. Sulpiride was observed to have a contraceptive effect at the usual doses employed to treat patients for psychiatric disorders, (100 to 1000 mg per day). It has not been used extensively as a contraceptive, however, because of the relatively high dosage required for satisfactory protection and because clinical tests have shown that protection is incomplete during the first two months of drug administration. (D. Buvat et al. Rev. Fr. Gynecol. Obstet. 71 (1) pp. 53–51).

The use of psychotropic substances for contraceptive purposes has previously been recommended only in the form of local application as illustrated, for example in PCT publication Nos. 81/03421 and 83/00086 issued to Cormier, which describe preparations for intra-vaginal or intra-uterine use. These preparations include a psychotropic derivative, such as a phenothiazine or benzodiazepine, which is employed as a foam, jelly, or other conventional pharmaceutical vehicle for external use. In principle, the usual spermicidal compound is combined with or replaced by a psychotropic substance, which penetrates the spermatozoon membrane and inhibits spermatozoon activation by calmoduline, thus blocking the spermatozoon's fertilizing action.

It is known to use progestogens for contraceptive purposes. A distinction is made between three types of contraceptive use:

(1) Daily use at very low doses

At low doses, progestogens modify the cervical mucus and thus prevent spermatozoa from entering the cervix. Use of progestogens at these doses, however, also interferes with gonadotrophin secretion (FSH and LH), giving rise to the following therapeutic disadvantages:

incomplete contraceptive effect, particularly at the beginning of treatment;
intermittent break-through bleeding; and
suppression of withdrawal bleeding, obtained with intermittently administered treatment required to preserve the psychological comfort of recurring "menstrual" cycles. Norgestrel used at a rate of 30 micrograms per day or norethindrone used at a rate of 300 micrograms per day are typical examples of daily low-dose progestagen therapy.

(2) Use for 21 days per cycle at high doses

The contraceptive effect achieved by progestogens administered according to this treatment schedule results from inhibition of gonadrotophin secretion, as, for example, with 2 mg of ethynodiol diacetate daily for 21 days. Such treatment has disadvantages and may induce severe endometrial atrophy, with remitting metrorrhagia or absence of "menstruation" between courses of treatment. In addition, the clinical tolerance of this method is judged to be too highly uncertain.

(3) Use in "depot" form

Contraception is achieved by monthly injections of medroxyprogesterone acetate (known for example under the trade name DEPO-PROVERA). Progesterone administered in this way presents the following disadvantages which are non-reversible as long as the effect of the injection persists:

disappearance of the "menstrual" cycle;
irregular or prolonged bleeding; and
uncertainty with respect to the time at which fertility is restored after treatment is discontinued.

It is also well known that a number of contraceptive preparations combine a progestogen and an estrogen generally ethinyl-estradiol). The estrogens contained in such combinations, however, are considered to cause certain metabolic disturbances and hepatic or thromboembolic accidents. Consequently, this type of contraception is not feasible in all situations due to the risks of estrogen therapy or its contra-indication in certain patients.

SUMMARY OF THE INVENTION

Therefore, in accordance with the present invention, a new pharmaceutical composition for suppressing fertility, including a progestogen and a benzamide, is proposed which provides effective contraception from the onset of treatment at low dosage levels, thereby providing a considerable reduction in side effects. This therapeutic composition includes: a prolactin-elevating benzamide, a progestogen and a pharmaceutically acceptable carrier.

The factors to be taken into account in selecting the benzamide of the invention include its weak effect on the central nervous system and its strong peripheral and, in particular, endocrinal effects. The benzamide should also exhibit no catatonic effect and should exhibit potency at low doses to inhibit estrus, which, in turn, reflects their strong impact on the hypothalamo-hypophysial axis.

In breast-feeding mothers, lactation determines a period of infertility with total ovarian inactivity, which is very marked initially. Subsequently, suckling frequency decreases (with a consequent reduction in suckling-induced stimuli) resulting in a period of relative infertility with resumption of ovarian activity characterized by an abnormal luteal phase. The mechanism of such infertility is still subject to speculation, but the rise in prolactin, secondary to suckling, has been suggested as one of the causes.

Prolactin may act on the hypothalamus by suppressing the positive feedback of estrogens responsible for ovulation, and inversely by facilitating negative feedback on gonadotrophin secretion. Prolactin may act directly on the ovary and inhibit the action of gonadotrophins on follicular growth resulting in subsequently abnormal luteal phases, characterized by poor follicular development (McNeilly et al. J. Reprod. Fert. (1982) 65, 559–569).

The hypofertility caused by certain benzamides is probably partly due to their hyperprolactinemic effect. However, it may be that their estrus blocking effect does not only depend on the serum concentration of prolactin, but also on inhibition of LH-RH secretion. Such a mechanism has been put forward by Hermand et coll. (L'Encephale 1975—I, 375-382).

DETAILED DESCRIPTION OF THE INVENTION

In general, benzamides of the structural formula I may be employed.

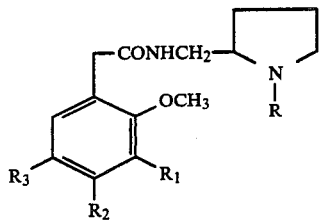
(I)

wherein R is an alkyl group having 1 to 3 carbon atoms, an allyl group, or a cycloalkylalkyl group; $R_1$ is hydrogen or methoxy; $R_2$ is hydrogen or amino and $R_3$ is sulfamoyl, methylsulfamoyl, or alkylsulfonyl, wherein at least one of $R_1$ or $R_2$ is hydrogen.

Typical benzamides include N-[(1-allyl 2-pyrrolidinyl) methyl]2,3-dimethoxy 5-sulfamoyl benzamide; N-[(1-ethyl 2-pyrrolidinyl)methyl]2-methoxy 4-amino 5-ethylsulfonyl benzamide; N-[(1-allyl 2-pyrrolidinyl) methyl]2-methoxy 4-amino 5-methyl-sulfamoyl benzamide and N-[(1-methyl 2-pyrrolidinyl)methyl]2-methoxy 4-amino 5-ethylsulfonyl benzamide. Sulpiride is a preferred benzamide, which, at a dose of 1 mg/kg increases the number of days of diestrus by more than 200%.

The potency of the benzamides of the present invention in inhibiting estrus at low doses is illustrated in Table I. In that Table the test results represent the increase in the number of diestrus in female rats compared to reference rats which did not receive the indicated benzamide at a dose of 1 mg/kg.

TABLE I

| Compound administered at 1 mg/kg | Increase in the number days of diestrus |
|---|---|
| 1 | +231% |
| 2 | +168% |
| 3 | +251% |
| 4 | +164% |
| 5 | +157% |

In the Table Compounds 1-5 were as follows:

| No. | Benzamide |
|---|---|
| 1 | Sulpiride |
| 2 | N—[(1-allyl 2-pyrrolidinyl) methyl] 2,3-dimethoxy 5-sulfamoyl benzamide |
| 3 | N—[(1-ethyl 2-pyrrolidinyl) methyl] 2-methoxy 4-amino 5-ethylsulfonyl benzamide |
| 4 | N—[(1-allyl 2-pyrrolidinyl) methyl] 2-methoxy 4-amino 5-methylsulfamoyl benzamide |
| 5 | N—(1-methyl 2-pyrrolidinyl) methyl] 2-methoxy 4-amino 5-ethylsulfonyl benzamide |

The progestogen of the invention is a progestogen which has been recognized as useful in contraception and is compatible with the benzamide of the invention. Such progestogens broadly include synthetic progestogens, especially of the nor-19 steroid series.

The preferred progestogens are lynestrenol, norethynodrel, norgesterone, norgestrel, ethynodiol diacetate, medroxyprogesterone and, especially, norethindrone. Such progestogens are well known to the art and their preparation and principles of use are well understood.

In addition a pharmaceutically acceptable carrier is employed. Such carriers are well known to the art. Typical carriers include starch, lactose, gelatine, magnesium stearate, polyoxyethyleneglycol and polyvinylpyrrolidone.

Clinical results have demonstrated the synergistic effect of the combination of a benzamide of the invention with a progestogen of the invention making it possible to use smaller doses of each of these constituents. For example, the daily dosage of sulpiride preferably ranges only from 5 to 25 mg, most preferably 10 mg, when associated with the progestogen. Further, the daily dosage of norethindrone, taken as an example of a progestogen of the invention, is preferably 5 to 250 micrograms when employed with a benzamide of the invention. Such dosages at their maximum, typically equal only half the usual daily doses of such contraceptive drugs and offer complete contraceptual protection with an increased margin of safety.

Accordingly for most contraceptive purposes the benzamides of the invention are employed in dosages of 5 to 30 mg and the progestogens of the invention are employed in dosages from about 5 to 300 micrograms.

Such compositions are of particular interest as a "starter pill" administered for 1 to 3 months at the beginning of contraception to overcome the disadvantages of the previously described contraceptives; i.e. ensuring immediate contraception and avoiding frequent breakthrough bleeding. Subsequently, conventional pure-progestogenic contraception could be utilized, once ovulation was completely inhibited.

The present composition of the invention is also of interest because of the possibility of using it in populations where the nursing period is prolonged, as in the case of female populations in developing countries. It is noteworthy that the estro-progestrogenic contraception that is presently recommended gradually reduces lactation and, paradoxically, causes premature restoration of fertility. This, along with the frequent poor compliance of patients taking estro-progestogenic contraception, results in an increase in birth rate.

In that context, a pharmaceutical composition which provides both reliable contraception and the maintenance of lactation is of special interest, particularly since breast-feeding and increased intervals between births constitute two main factors in the struggle against infantile mortality in developing nations.

In another embodiment of the invention the addition of a very small amount of an estrogen to the pharmaceutical composition of the invention results in a "physiological pill" i.e. a pill which preserves the impression of a normal menstrual cycle, whereby several days of "menstrual" bleeding occur in the week-long interim between 3-week treatment cycles. Consequently, in addition to the total contraceptive protection offered by this embodiment, at markedly reduced doses of the compounds involved, the patient has the benefit of the psychological comfort of having regular "menses" and will, as a result, be more likely to comply to therapy.

In general, conventionally employed estrogens are utilized in this aspect of the invention. A typical estrogen is ethinyl estradiol. Such estrogens can be employed in amounts up to about 50% of their conventional dosage. With ethinyl estradiol, up to about 15 micrograms are employed in the inventive compositions, as compared to the commercially utilized dosage of 30 micrograms. If desired, a synthetic progestogen with intrinsic estrogenic activity, such as lynestrenol, can be used as the progestogenic agent, thus eliminating the need for a separate estrogen compound.

The following examples are proposed in order to illustrate certain preferred embodiments of the invention but without limiting its scope:

EXAMPLE 1

Use of a Progestogen

The following ingredients are formulated into an inert tablet or capsule, using conventional tabletting or capsule manufacturing processes:

| | |
|---|---|
| Norethindrone | 150 ug |
| Sulpiride | 10 mg |
| excipient | qs 500 mg |

EXAMPLE 2

Use of a Progestogen with Estrogenic Activity

| | |
|---|---|
| Lynestrenol | 250 ug |
| Sulpiride | 10 mg |
| excipient | qs 500 mg |

EXAMPLE 3

Use of a Progestogen and an Estrogen

| | |
|---|---|
| Norgestrel | 15 ug |
| Sulpiride | 10 mg |
| Ethinyl-estradiol | 15 ug |
| excipient | qs 500 mg |

All the usual pharmaceutical forms, including capsules and tablets, among others, suitable for containing the substances according to the invention, may be used for the application thereof.

The duration of use will depend on the physician's prescription, but in general, a maximum of 3 months is recommended when the invention is to be used as a precursor to conventional pure-progestogenic contraception, whether the latter is administered daily (capsules or tablets) or as a long term depot injection (e.g. a monthly injection).

What is claimed is:

1. A pharmaceutical composition for suppressing fertility comprising a prolactin elevating benzamide, a progestogen and a pharmaceutically acceptable carrier.

2. The composition of claim 1 wherein the benzamide is sulpiride.

3. The composition of claim 2 in which sulpiride is employed in amounts from about 5 to 25 mg per unit dose.

4. The composition of claim 1 in which the progestogen is norethindrone.

5. The composition of claim 4 in which the norethindrone is employed in amounts from 5 to 250 micrograms.

6. The composition of claim 1 in which the progestogen is lynestrenol.

7. The composition of claim 1 including an estrogen.

8. The composition of claim 7 in which the estrogen is ethinyl-estradiol.

9. Process for treating a subject to inhibit ovulation prior to commencement of progestogenic contraception comprising administering a therapeutically effective dosage of a pharmaceutical composition comprising a prolactin elevating benzamide, a progestogen and a pharmaceutically acceptable carrier.

10. Process for suppressing fertility without inhibiting lactation by administering to a subject a therapeutically effective dosage of a contraceptive composition comprising a prolactin elevating benzamide, a progestogen and a pharmaceutically acceptable carrier.

* * * * *